United States Patent
Frid et al.

(10) Patent No.: US 6,305,371 B1
(45) Date of Patent: Oct. 23, 2001

(54) INHALATION FOR ADMINISTERING MEDICAMENT BY INHALATION

(75) Inventors: Per Frid, Lund (SE); Robert Jansen; Paul Wright, both of Leics (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/117,229
(22) PCT Filed: May 8, 1998
(86) PCT No.: PCT/SE98/00846
  § 371 Date: Jul. 24, 1998
  § 102(e) Date: Jul. 24, 1998
(87) PCT Pub. No.: WO98/51360
  PCT Pub. Date: Nov. 19, 1998

(30) Foreign Application Priority Data

May 12, 1997 (SE) ................................................... 9701750

(51) Int. Cl.[7] .......................... A61M 15/00; A61M 16/00
(52) U.S. Cl. ............................... 128/203.12; 128/200.14; 128/200.23
(58) Field of Search ....................... 128/200.14, 200.19, 128/200.23, 203.12, 203.13

(56) References Cited

U.S. PATENT DOCUMENTS

| | | | | |
|---|---|---|---|---|
| 3,636,949 | * | 1/1972 | Kropp ............................ | 128/203.15 |
| 4,765,348 | * | 8/1988 | Honeycutt ......................... | 131/273 |
| 5,135,141 | * | 8/1992 | Harmer et al. ...................... | 223/85 |
| 5,460,171 | * | 10/1995 | Pesenti et al. .................... | 128/200.14 |
| 5,533,498 | * | 7/1996 | Sioutas ............................ | 128/200.23 |
| 5,544,647 | * | 8/1996 | Jewett et al. ..................... | 128/200.23 |
| 5,704,344 | * | 1/1998 | Cole ................................ | 128/200.14 |
| 5,785,216 | * | 7/1998 | Gouldson et al. .................. | 223/85 |
| 5,797,392 | * | 8/1998 | Keldmann et al. ............. | 128/203.15 |
| 5,814,252 | * | 9/1998 | Gouldson et al. .................. | 264/40.5 |
| 5,839,429 | * | 11/1998 | Marnfeldt et al. .............. | 128/200.14 |
| 5,941,241 | * | 8/1999 | Weinstein et al. .............. | 128/200.14 |
| 5,975,127 | * | 11/1999 | Dray ..................................... | 137/495 |
| 6,085,950 | * | 7/2000 | Gouldson et al. .................... | 223/85 |

FOREIGN PATENT DOCUMENTS

| | | |
|---|---|---|
| 0 360 463 | 3/1990 | (EP) . |
| 91/19524 | 12/1991 | (WO) . |
| 96/26755 | 9/1996 | (WO) . |

\* cited by examiner

*Primary Examiner*—John G. Weiss
*Assistant Examiner*—Joseph F. Weiss, Jr.
(74) *Attorney, Agent, or Firm*—Nixon & Vanderhye

(57) ABSTRACT

An inhaler for administering medicament by inhalation and a method of manufacturing a housing of the same, the inhaler including a housing formed as a single-piece moulding having a first portion (18) which, in normal use, comes into contact with medicament and the mouth or nose of a user through which medicament is inhaled and a second portion (20) which defines at least part of the outer surface of the housing and, in normal use, does not come into contact with medicament or the mouth or nose of a user through which medicament is inhaled, wherein the material constitution of at least part of the second portion (20) defining at least part of the outer surface of the housing is different to the material constitution of the first portion (18).

13 Claims, 3 Drawing Sheets

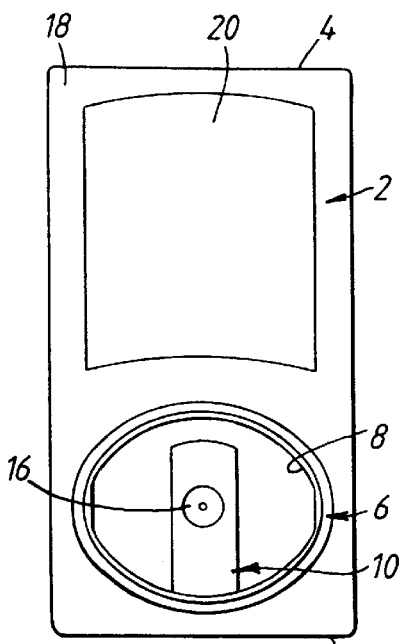
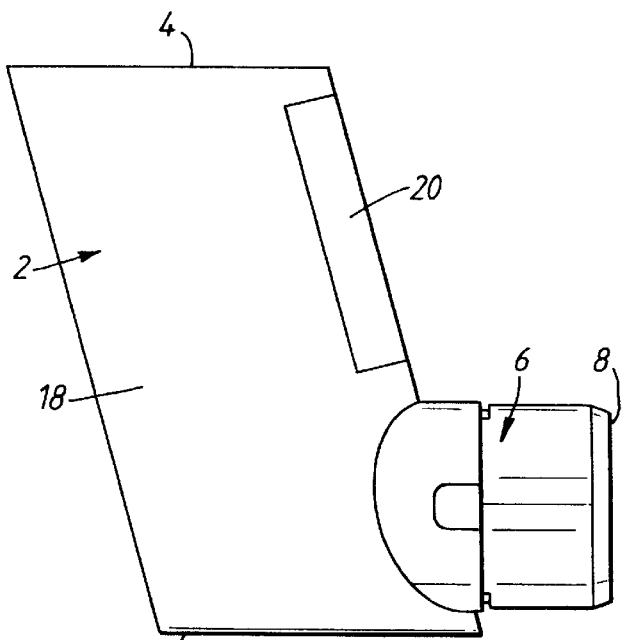
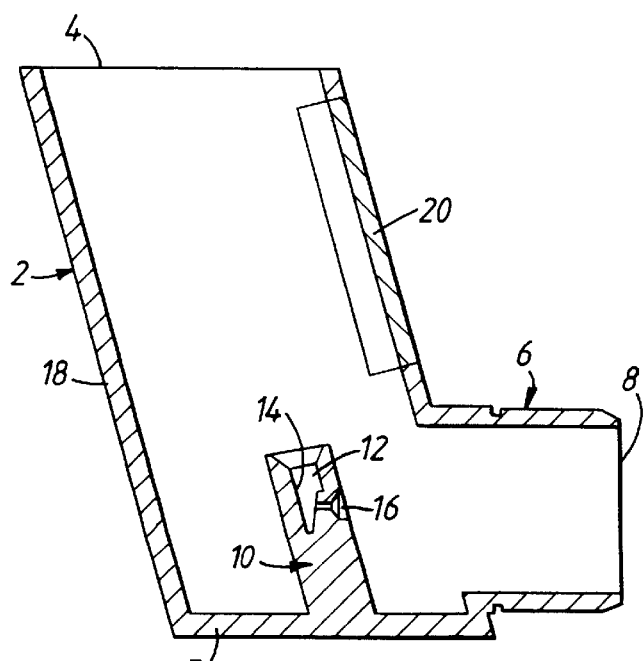

INHALATION FOR ADMINISTERING MEDICAMENT BY INHALATION

The present invention relates to an inhaler for administering medicament by inhalation and a method of manufacturing a housing of the same.

BACKGROUND OF THE INVENTION

Various kinds of inhaler are known for delivering metered doses of medicament for inhalation. Typically, pressurized liquid systems and dry powder systems are used to deliver medicament to a patient. In one pressurized liquid system a liquid containing medicament is stored in a pressurized container and a metered dose is delivered as an aerosol by a pressurized metered dose inhaler. In dry powder systems powder containing medicament is stored in individual blisters, on tape or in bulk in a chamber and a metered dose is provided by a dry powder inhaler.

All such inhalers include parts which come into contact with medicament and parts, some in common with the parts which come into contact with medicament, which come into contact with the mouth or nose of a user. It will be appreciated that it is important to ensure that those parts do not have any adverse effect on either the medicament or the user.

It is an aim of the present invention to provide an improved inhaler and a method of manufacturing a housing of the same in view of this requirement.

SUMMARY OF THE INVENTION

Accordingly, the present invention provides an inhaler for administering medicament by inhalation, including a housing formed as a single-piece molding having a first portion which, in normal use, comes into contact with medicament and the mouth or nose of a user through which medicament is inhaled and a second portion which defines at least part of the outer surface of the housing and, in normal use, does not come into contact with medicament or the mouth or nose of a user through which medicament is inhaled, wherein the material constitution of at least part of the second portion defining at least part of the outer surface of the housing is different to the material constitution of the first portion.

The at least part of the second portion can have many different material constitutions, for instance in including a coloring pigment for identifying the medicament to be administered and/or being formed of a rubberized material to provide for improved grip.

In this way, a range of housings having a single basic design can be developed for use with different medicaments. This approach has the particular advantage that, because the second portion of each of the housings does not come into contact with medicament or the mouth or nose of a user and the first portion of each of the housings is formed of the same material, in many countries throughout the world it is only be necessary to obtain regulatory approval for one housing in the entire range.

Preferably, other than a coloring pigment in the at least part of the second portion, the first and second portions have generally the same material constitution. Where the first and second portions are formed of polymeric materials, those portions are in a preferred embodiment formed of the same polymeric material even if of a different grade. In this way, the molding of the housing is simplified, since the first and second portions of the housing will bond together more readily and the problems associated with using materials having different thermal expansion characteristics are avoided. In practice, the coloring pigment in the at least part of the second portion is conveniently provided from a master batch which includes pigment, a polymer base or carrier (which may be different to the basic polymeric material of the first and second portions) and processing aids such as lubricants and dispersion agents.

Preferably, the first portion has a relatively simple material constitution, in particular without a coloring pigment. In this way, the risk of chemical leaching from the first portion is minimized.

The present invention also provides a method of manufacturing a housing of an inhaler for administering medicament by inhalation having a first portion which, in normal use, comes into contact with medicament and the mouth or nose of a user through which medicament is inhaled and a second protion which defines at least part of the outer surface of the housing and, in normal use, does not come into contact with medicament or the mouth or nose of a user through which medicament is inhaled, the method comprising the step of molding the first and second portions as a single piece, wherein at least part of the second portion defining at least part of the outer surface of the housing is formed of a material of different constitution to that of the first portion.

Preferably, the material for the at least part of the second portion is successively introduced into a mold with respect to the material for the first portion and the remainder of the second portion.

Alternatively, the housing may be moulded by insert molding. That is, material is introduced into a first mold to form part of the housing and then that part is transferred to another mold into which another material is introduced to complete the housing. In this way, the first portion of the housing which comes into contact both with medicament and the mouth or nose of a user is formed of a material suited for the medical purpose and for which regulatory approval has already been obtained, whilst the at least part of the second portion is formed from another material of different constitution.

By providing the housing as a single-piece molding the housing is more robust than a housing formed of separate components. Moreover, it is impossible for a user to tamper with the housing. If the first and second portions of the housing were to be provided by separate components it would be open to a user to interchange parts from one housing for use with one medicament with parts from another housing for use with another medicament which would lead to cross-contamination. Furthermore, the housing is less expensive to manufacture as a single-piece molding than as separate moldings which would have to be assembled.

The present invention recognises for the first time that multi-part molding techniques may be applied in this field with particular advantages, specifically relating to the conflicting demands of material contact with medicament and the mouth or nose of a user in some parts of the housing and desired variation in other parts of the housing.

It will be appreciated that the method of manufacture of the present invention is not limited to two-stage molding and the housing may have many parts formed integrally from different material constitutions.

In a preferred embodiment the inhaler is a pressurized metered dose inhaler and the housing is the actuator of the pressurized metered dose inhaler.

BRIEF DESCRIPTION OF THE DRAWINGS

Preferred embodiments of the present invention will now be described hereinbelow by way of example only with reference to the accompanying drawings, in which:

FIGS. 4 to 6 illustrate front, side and vertical sectional views of an actuator of a pressurized metered dose inhaler in accordance with a second embodiment of the present invention.

DETAILED DESCRIPTION OF PREFERRED EMBODIMENTS

Figure 1:
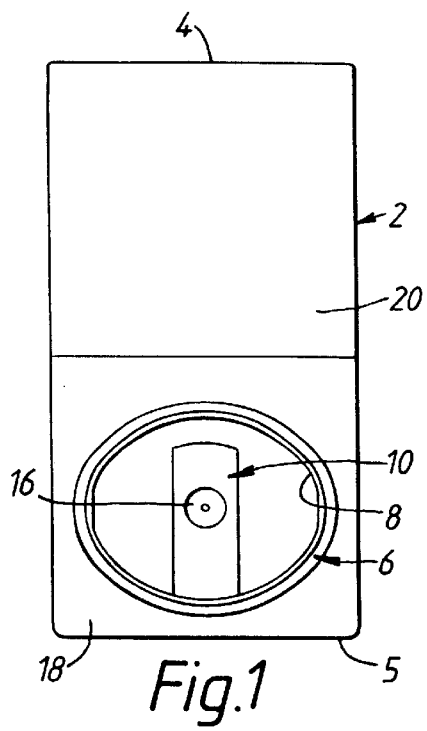
FIGS. 1 to 3 illustrate front, side and vertical sectional views of an actuator of a pressurized metered dose inhaler in accordance with a first embodiment of the present invention.
Figure 2:
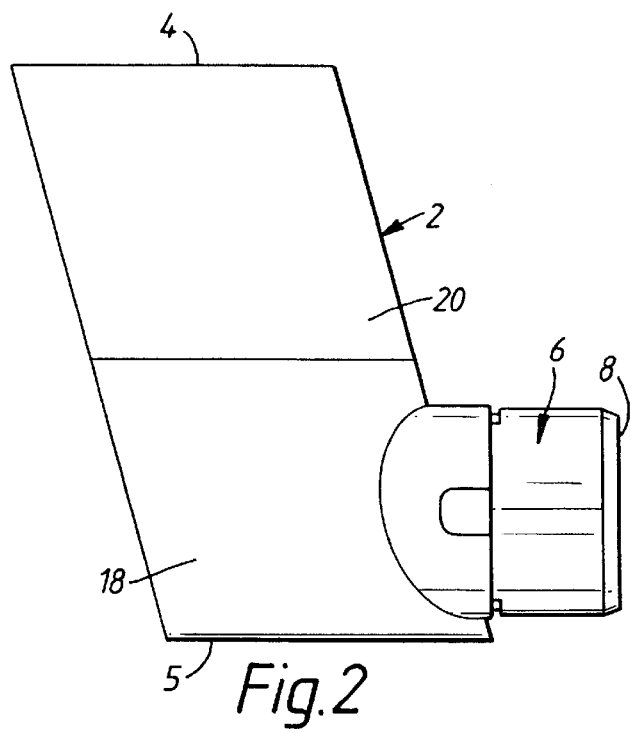
Figure 3:
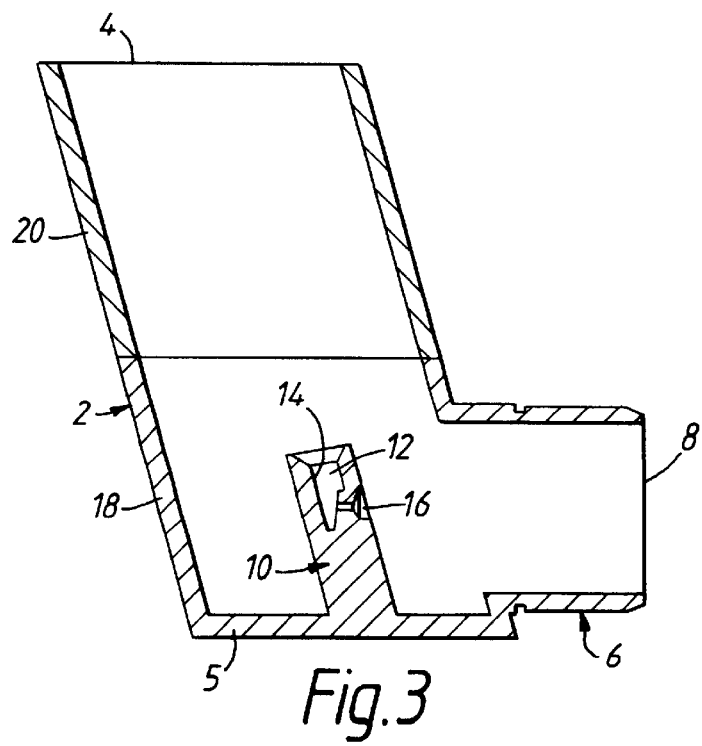

FIGS. 1 to 3 illustrate an housing of a pressurized metered dose inhaler in accordance with a first embodiment of the present invention. The housing comprises a first, main tubular section 2, one, the upper, end of which is open and provides an opening 4 into which a container (not illustrated), in this embodiment an aerosol canister having a valve stem, is in use inserted and the other, lower, end of which is closed by a wall member 5.

The housing further comprises a second tubular section 6 which extends substantially laterally from the other, that is, the lower, end of the main tubular section 2; the second tubular section 6 acting as a mouthpiece which is in use gripped in the lips of a user and having an opening 8 at the distal end thereof through which medicament is in use inhaled. The housing still further comprises a nozzle block 10 which extends upwardly from the wall member 5 into the main tubular section 2. The nozzle block 10 includes a tubular bore 12 which is located on the longitudinal axis of the main tubular section 2. One, the upper, end of the tubular bore 12 is open and provides an opening 14 into which is received the valve stem of a container. The other, lower, end of the tubular bore 12 includes a laterally-directed spray orifice 16 which is configured to direct a spray into the second tubular section 6. The housing is integrally formed as a single-piece molding, first and second portions 18, 20, in this embodiment essentially lower and upper halves, of which are formed of polymeric materials of different constitution. Typically, the material of the second portion 20 includes a coloring pigment representative of the medicament with which the housing is to be used. In coloring a part of the housing with a pigment specific to the medicament with which it is to be used cross-contamination of medicaments can be avoided.

In use, with an aerosol canister fitted in the housing, a user grips the mouthpiece provided by the second tubular section 6 in his/her lips. The user then depresses the base of the canister which extends out of or is at least close to the opening 4 in the main tubular section 2 so as to release a dose of medicament from the aerosol canister and at the same time inhales so as to inhale the dose of medicament.

FIGS. 4 to 6 illustrate an housing of a pressurized metered dose inhaler in accordance with a second embodiment of the present invention. This housing is almost identical in construction to the actuator of the inhaler of the above-described first embodiment. For this reason, and in order to avoid unnecessary duplication of description, only the constructional differences will be mentioned and reference should be made to the preceding description. The housing of this embodiment differs from the actuator of the above-described first embodiment only in that the first and second portions 18, 20 are differently configured. In this embodiment the second portion 20 is formed as a panel in the main tubular section 2. In a preferred embodiment the panel provided by the second portion 20 includes printed information, for instance as a transparent decal with opaque lettering.

Figure 7:
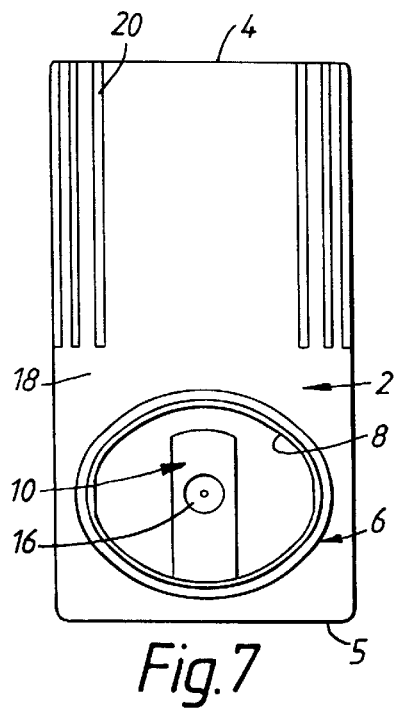
FIGS. 7 to 9 illustrate front, side and vertical sectional views of an actuator of a pressurized metered dose inhaler in accordance with a third embodiment of the present invention.
Figure 8:
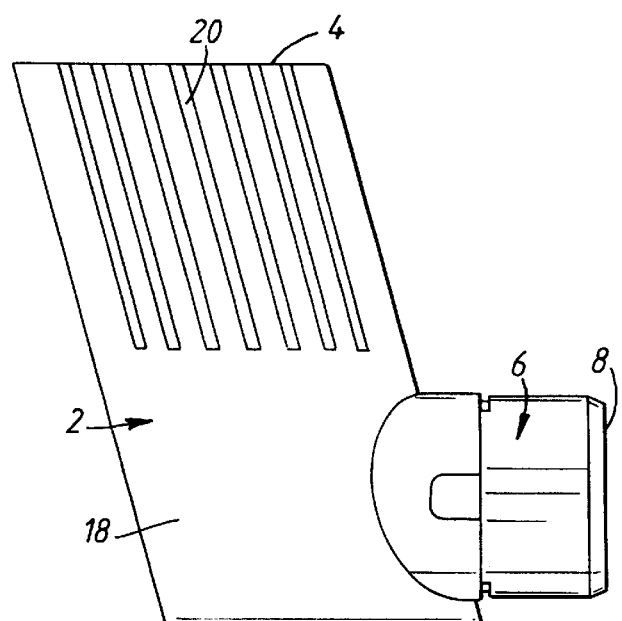
Figure 9:
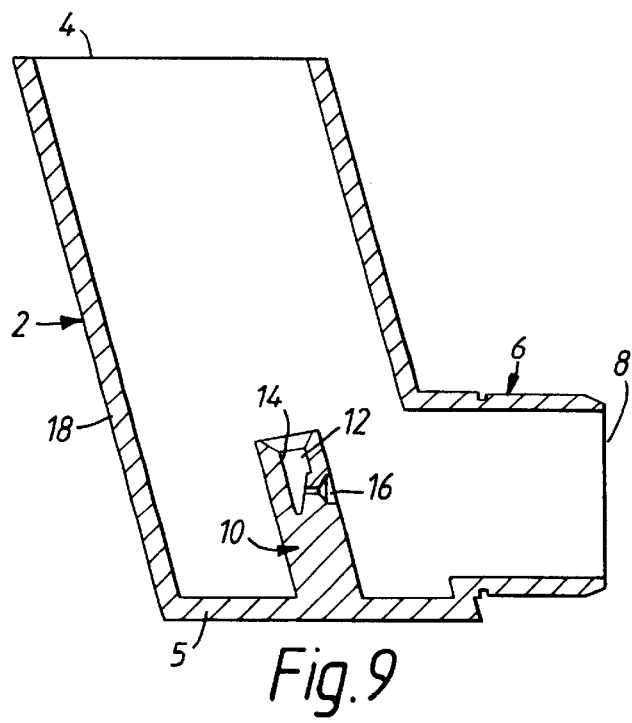

FIGS. 7 to 9 illustrate an actuator of a pressurized metered dose inhaler in accordance with a third embodiment of the present invention. This housing is almost identical in construction to the housing of the inhaler of the above-described first embodiment. For this reason, and in order to avoid unnecessary duplication of description, only the constructional differences will be mentioned and reference should be made to the preceding description. The housing of this embodiment differs from the actuator of the above-described first embodiment only in that the first and second portions 18, 20 are differently configured. In this embodiment the second portion 20 is formed as a series of substantially axially-directed strips in the main tubular section 2. In a preferred embodiment the strips provided by the second portion 20 are formed of a rubberized material to assist the user in gripping the actuator.

Finally, it will be understood by a person skilled in the art that the present invention has been described in its preferred embodiments and can be modified in many different ways without departing from the scope of the present invention as defined by the appended claims.

What is claimed is:

1. An inhaler for administering medicament by inhalation, including a housing formed as a single-piece molding having a first portion which, in normal use, is contactable with medicament and a mouth or nose of a user through which medicament is inhaled and a second portion which defines at least part of an outer surface of the housing and, in normal use, is not contactable with medicament or a mouth or nose of a user through which medicament is inhaled, at least part of the second portion defining at least part of the outer surface of the housing having a material constitution which is different to the material constitution of the first portion to allow identification of the medicament to be administered.

2. The inhaler according to claim 1, wherein the at least part of the second portion includes a coloring pigment for identifying the medicament to be administered.

3. The inhaler according to claim 2, wherein, other than including a coloring pigment, the at least part of the second portion has generally the same material constitution as the first portion.

4. The inhaler according to any of claim 1, wherein the inhaler is a pressurized metered dose inhaler and the housing includes means for releasing a dose of medicament.

5. The inhaler according to claim 4, wherein said means comprises a nozzle block having a spray orifice configured to direct a spray into said first portion.

6. An inhaler for administering medicament by inhalation, comprising:

a housing formed as a single-piece molding having a first portion which, in use, is contactable with medicament and a mouth or nose of a user;

a second portion which defines at least part of an outer surface of said housing and, in use, is not contactable with medicament or a mouth or nose of a user through which medicament is inhaled;

at least part of the second portion defining at least part of the outer surface of the housing having a material constitution which is different to the material constitution of the first portion to allow identification of the medicament to be administered.

7. A method of manufacturing a housing of an inhaler for administering medicament by inhalation having a first portion which, in normal use, is contactable with medicament and a mouth or nose of a user through which medicament is inhaled and a second portion which defines at least part of an outer surface of the housing and, in normal use, is not contactable with medicament or a mouth or nose of a user through which medicament is inhaled, the method comprising the step of molding the first and second portions as a single piece, at least part of the second portion defining at least part of the outer surface of the housing being formed of a material of different constitution to that of the first portion to allow identification of the medicament to be administered.

8. The method according to claim 7, wherein the material for the at least part of the second portion is successively introduced into a mould with respect to the material for the first portion and the remainder of the second portion.

9. The method according to claim 7, wherein the least part of the second portion (20) includes a colouring pigment for identifying the medicament to be administered.

10. The method according to claim 9, wherein, other than including a coloring pigment, the at least part of the second portion has generally the same material constitution as the first portion.

11. The method according to claim 7, wherein the inhaler is a pressurized metered dose inhaler and the housing includes means for releasing a dose of medicament.

12. The method according to claim 11, wherein said means includes a nozzle block having a spray orifice configured to direct a spray into said first portions.

13. A method of manufacturing a housing of an inhaler for administering medicament by inhalation having a first portion which, in use, is contactable with medicament and a mouth or nose of a user through which medicament is inhaled and a second portion which defines at least part of an outer surface of the housing and, in use, is not contactable with medicament or a mouth or nose of a user, said method comprising molding said first and second portions as a single piece, at least part of the second portion defining at least part of the outer surface of the housing being formed of a material of different constitution to that of the first portion to allow identification of the medicament to be administered.

* * * * *